United States Patent
Fruchey et al.

(10) Patent No.: US 9,115,080 B2
(45) Date of Patent: *Aug. 25, 2015

(54) PROCESSES FOR PRODUCING CAPROLACTAM AND DERIVATIVES THEREOF FROM FERMENTATION BROTHS CONTAINING DIAMMONIUM ADIPATE OR MONOAMMONIUM ADIPATE

(76) Inventors: Olan S. Fruchey, Hurricane, WV (US); Leo E. Manzer, Wilmington, DE (US); Dilum Dunuwila, Princeton, NJ (US); Brian T. Keen, Pinch, WV (US); Brooke A. Albin, Charleston, WV (US); Nye A. Clinton, Hurricane, WV (US); Bernard D. Dombek, Charleston, WV (US)

( * ) Notice: Subject to any disclaimer, the term of this patent is extended or adjusted under 35 U.S.C. 154(b) by 247 days.

This patent is subject to a terminal disclaimer.

(21) Appl. No.: 13/701,622

(22) PCT Filed: Jun. 10, 2011

(86) PCT No.: PCT/US2011/039895
§ 371 (c)(1),
(2), (4) Date: Jan. 28, 2013

(87) PCT Pub. No.: WO2011/159555
PCT Pub. Date: Dec. 22, 2011

(65) Prior Publication Data
US 2013/0131306 A1 May 23, 2013

Related U.S. Application Data

(60) Provisional application No. 61/355,197, filed on Jun. 16, 2010.

(51) Int. Cl.
*C07D 223/10* (2006.01)
*C12P 7/44* (2006.01)
*C12P 17/10* (2006.01)
*C07D 201/08* (2006.01)

(52) U.S. Cl.
CPC ............ *C07D 201/08* (2013.01); *C07D 223/10* (2013.01); *C12P 7/44* (2013.01); *C12P 17/10* (2013.01)

(58) Field of Classification Search
CPC .... C07D 201/08; C07D 223/10; C12P 17/10; C12P 7/44
USPC .............................. 528/323; 540/538; 435/121
See application file for complete search history.

(56) References Cited

U.S. PATENT DOCUMENTS

| | | | |
|---|---|---|---|
| 4,400,468 A | 8/1983 | Faber | |
| 4,480,034 A | 10/1984 | Hsieh | |
| 5,487,987 A | 1/1996 | Frost et al. | |
| 5,616,496 A | 4/1997 | Frost et al. | |
| 6,479,620 B1 * | 11/2002 | Fergusson et al. | 528/310 |
| 6,794,165 B2 | 9/2004 | Cheng et al. | |
| 6,958,381 B2 | 10/2005 | Winterling et al. | |
| 7,427,684 B2 * | 9/2008 | Crabtree et al. | 548/400 |
| 8,703,900 B2 * | 4/2014 | Fruchey et al. | 528/323 |
| 2009/0305364 A1 | 12/2009 | Burgard et al. | |
| 2011/0269993 A1 * | 11/2011 | Fruchey et al. | 562/593 |

FOREIGN PATENT DOCUMENTS

| | | | |
|---|---|---|---|
| CN | 1827579 A | | 9/2006 |
| DE | 27 18 363 | | 10/1978 |
| GB | 778 253 A | | 7/1957 |
| GB | 778253 | | 7/1957 |
| JP | 49-19250 A | | 2/1974 |
| JP | 2007-254354 | * | 10/2007 |
| JP | 2008-144075 A | | 6/2008 |
| WO | 2006/069110 A2 | | 6/2006 |
| WO | 2009/113853 A2 | | 9/2009 |
| WO | 2010/003728 A1 | | 1/2010 |

OTHER PUBLICATIONS

Translation of JP2007254354, 2007.*
Okuhara, M. et al., "Formation of Glutaric and Adipic Acids from n-Alkanes with Odd and Even Numbers of Carbons by *Candida tropicalis* OH23," *Agr. Biol. Chem.*, 1971, vol. 35, No. 9, pp. 1376-1380.
Draths, K.M. et al., "Environmentally Compatible Synthesis of Adipic Acid from D-Glucose," *J. Am. Chem. Soc.*, 1994, vol. 116, pp. 399-400 (printout—1 sheet).
Niu, W. et al., Benzene-Free Synthesis of Adipic Acid, *Biotechnol. Prog.*, Mar.-Apr. 2002, vol. 18, No. 2, pp. 201-211.
L. McMaster, "The Preparation and Properties of the Neutral Ammonium Salts of Organic Acids," *Journal of the American Chemical Society*, vol. 36, 1914, pp. 742-747.
Brehmer, B. et al., "Maximum fossil fuel feedstock replacement potential of petrochemicals via biorefineries," *Chemical Engineering Research and Design*, vol. 87, 2009, pp. 1103-1119.
Chinese Office Action dated Sep. 16, 2013, with explanatory letter in English dated Oct. 8, 2013.

* cited by examiner

*Primary Examiner* — Paul A Zucker
*Assistant Examiner* — Mark Luderer
(74) *Attorney, Agent, or Firm* — IP Group of DLA Piper LLP

(57) ABSTRACT

Processes for producing caprolactam (CL) and derivatives thereof from adipic acid (AA) obtained from fermentation broths containing diammonium adipate (DAA) or monoammonium adipate (MAA).

11 Claims, 3 Drawing Sheets

US 9,115,080 B2

PROCESSES FOR PRODUCING CAPROLACTAM AND DERIVATIVES THEREOF FROM FERMENTATION BROTHS CONTAINING DIAMMONIUM ADIPATE OR MONOAMMONIUM ADIPATE

RELATED APPLICATIONS

This is a §371 of International Application No PCT; US2011/039895, with an international filing date of Jun. 10, 2011(WO 2011/159555 A1, published Dec. 22, 2011), which is based on U.S. Patent Application No. 61/355,197 filed Jun. 16, 2010, the subject matter of which is incorporated herein by reference.

This disclosure contains a Sequence Listing which has been submitted in ASCII format via EFS-Web and is herb incorporated b reference in its entirely. Said ASCII copy created on Jan. 16, 2013, is named DN1064US.txt and is 7,551 bytes in size.

TECHNICAL FIELD

This disclosure relates to processes for producing caprolactam (CL) from fermentation broths diammonium adipate (DAA) or monoammonium adipate (MAA).

BACKGROUND

Certain carbonaceous products of sugar fermentation are seen as replacements for petroleum-derived materials for use as feedstocks for the manufacture of carbon-containing chemicals. One such product is adipic acid (AA). Given such a process for the direct production of substantially pure AA from a DAA-containing fermentation broth or MAA-containing fermentation broth and the possible use of such pure AA as a source material for the production of CL, it could be helpful to provide processes for producing CL and derivatives thereof in an economic and environmentally friendly way.

SUMMARY

We provide a process for producing CL from a clarified DAA-containing fermentation broth or MAA-containing fermentation broth including distilling the broth under super atmospheric pressure at a temperature of >100° C. to about 300° C. to form an overhead that comprises water and ammonia, and a liquid bottoms that comprises AA and at least about 20 wt % water, cooling and/or evaporating the bottoms to attain a temperature and composition sufficient to cause the bottoms to separate into a liquid portion and a solid portion that is substantially pure AA, separating the solid portion from the liquid portion, and contacting at least a part of the solid portion with hydrogen, optionally in the presence of a solvent, in the presence of a hydrogenation catalyst and an ammonia source, at a temperature of about 25° C. to about 500° C. and a pressure of about 0.5 to about 40 MPa to produce the CL.

We also provide a process for producing CL from a clarified DAA-containing fermentation broth or MAA-containing fermentation broth including adding an ammonia separating solvent and/or a water azeotroping solvent to the broth, distilling the broth at a temperature and pressure sufficient to form an overhead that comprises water and ammonia, and a liquid bottoms that comprises AA and at least about 20 wt % water, cooling and/or evaporating the bottoms to attain a temperature and composition sufficient to cause the bottoms to separate into a liquid portion and a solid portion that is substantially pure AA, separating the solid portion from the liquid portion, and contacting at least a part of the solid portion with hydrogen, optionally in the presence of a solvent, in the presence of a hydrogenation catalyst and an ammonia source, at a temperature of about 25° C. to about 500° C. and a pressure of about 0.5 to about 40 MPa to produce the CL.

DETAILED DESCRIPTION

Figure 1:
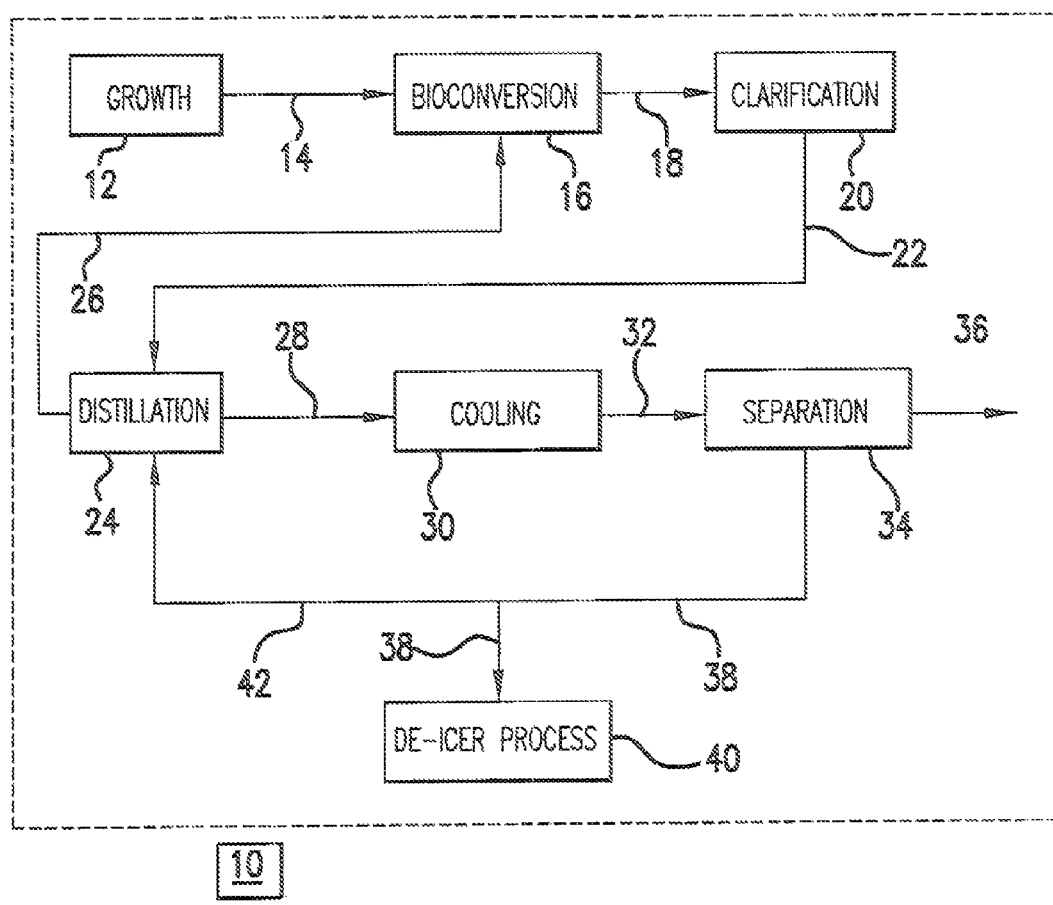
FIG. 1 is a block diagram of a process for making AA from a DAA-containing fermentation broth or a MAA-containing fermentation broth.

It will be appreciated that at least a portion of the following description is intended to refer to representative examples of processes selected for illustration in the drawings and is not intended to define or limit the disclosure, other than in the appended claims.

Our processes may be appreciated by reference to FIG. 1, which shows in block diagram form one representative example, 10, of our methods.

A growth vessel 12, typically an in-place steam sterilizable fermentor, may be used to grow a microbial culture (not shown) that is subsequently utilized for the production of the DAA, MAA and/or AA-containing fermentation broth. Such growth vessels are known in the art and are not further discussed.

The microbial culture may comprise microorganisms capable of producing AA from fermentable carbon sources such as carbohydrate sugars. Representative examples of microorganisms include *Escherichia coli* (*E. coli*), *Aspergillus niger*, *Corynebacterium glutamicum* (also called *Brevibacterium flavum*), *Enterococcus faecalis*, *Veillonella parvula*, *Actinobacillus succinogenes*, *Paecilomyces varioti*, *Saccharomyces cerevisiae*, *Candida tropicalis*, *Bacteroides fragilis*, *Bacteroides ruminicola*, *Bacteroides amylophilus*, *Lebsiella pneumonae* mixtures thereof and the like.

Preferred microorganisms include the *Candida tropicalis* (Castellani) Berkhout, anamorph strain OH23 having ATCC accession number 24887, *E. coli* strain AB2834/pKD136/pKD8.243A/pKD8.292 having ATCC accession number 69875, the *E. coli* cosmid clones designated 5B12, 5F5, 8F6 and 14D7 comprising a vector expressing the cyclohexanone monoxygenase having the amino acid sequence shown in SEQ ID NO: 2 and encoded by SEQ ID NO: 1 from *Acinetobacter* strain SE19, and the yeast strain available from Verdezyne, Inc. (Carslbad, Calif., USA; hereinafter "Verdezyne Yeast") which produces AA from alkanes and other carbon sources.

Fermentation broths containing AA can be produced from the *Candida tropicalis* (Castellani) Berkhout, anamorph strain OH23 having ATCC accession number 24887 by culture at 32° C. in a liquid medium containing 300 mg of $NH_4H_2PO_4$, 200 mg of $KH_2PO_4$, 100 mg of $K_2HPO_4$, 50 mg of $MgSO_4 \cdot 7H_2O$, 1 µg of biotin, 0.1% (w/v) yeast extract and about 1% (v/v) n-hexadecane in 100 ml of distilled water. Other culture media such as YM broth containing n-hexadecane may also be used. The procedure for producing fermentation broths containing AA from media containing n-hexadecane by culturing *Candida tropicalis* (Castellani) Berkhout, anamorph strain OH23 having ATCC accession number 24887 is also described in Okuhura et al., 35 Agr. Biol. Chem. 1376 (1971) the subject matter of which is incorporated herein by reference.

Fermentation broths containing AA can also be produced from E. coli strain AB2834/pKD136/pKD8.243A/pKD8.292 having ATCC accession number 69875. This can be done as follows. One liter of LB medium (in 4 L Erlenmeyer shake flask) containing IPTG (0.2 mM), ampicillin (0.05 g), chloramphenicol (0.02 g) and spectinomycin (0.05 g) can be inoculated with 10 mL of an overnight culture of E. coli strain AB2834/pKD136/pKD8.243A/pKD8.292 cells grown at 250 rpm for 10 h at 37° C. The cells can be harvested, resuspended in 1 L of M9 minimal medium containing 56 mM D-glucose, shikimic acid (0.04 g), IPTG (0.2 mM), ampicillin (0.05 g), chloramphenicol (0.02 g) and spectinomycin (0.05 g). The cultures can then be returned to 37° C. incubation. After resuspension in minimal medium the pH of the culture can be closely monitored, particularly over the initial 12 h. When the culture reaches a pH of 6.5, 5N NaOH or an appropriate amount of another base such as ammonium hydroxide can be added to adjust the pH back to approximately 6.8. Over the 48 h accumulation period, the culture should not allowed to fall below pH 6.3. After 24 h in the medium 12 mM cis, cis-muconate and 1 mM protocatechuate may be detected in the culture supernatant along with 23 mM D-glucose. After 48 h in the medium E. coli strain AB2834/pKD136/pKD8.243A/pKD8.292 cells can essentially replace the 56 mM D-glucose in the medium with 17 mM cis, cis-muconate.

The reduction of microbially synthesized cis, cis-muconate AA to produce a fermentation broth containing AA can then proceed as follows. Fifty milligrams of platinum on carbon (10%) can be added to 6 mL of a cell-free culture supernatant from the fermentation containing about 17.2 mM cis, cis-muconate. This sample can then be hydrogenated at 50 psi hydrogen pressure for 3 h at room temperature to produce a fermentation broth containing AA. The fermentation broth produced in this fashion may contain, for example, about 15.1 mM AA. The procedure for producing fermentation broths containing AA by culturing E. coli strain AB2834/pKD136/pKD8.243A/pKD8.292 cells by culture in a growth medium comprising D-glucose is also described in Draths & Frost, 116 J. Am. Chem. Soc. 399 (1994); Draths and Frost, 18 Biotechnol. Prog. 201 (2002); U.S. Pat. Nos. 5,487,987 and 5,616,496 the subject matter of which is incorporated herein by reference.

Fermentation broths containing AA can also be produced from the E. coli cosmid clones designated 5B12, 5F5, 8F6 and 14D7 comprising a vector expressing the cyclohexanone monooxygenase SEQ ID NO: 2 encoded by SEQ ID NO: 1 from Acinetobacter strain SE19 by culturing these clones in M9 minimal medium supplemented with 0.4% glucose as the carbon source. Cells can be grown at 30° C. with shaking for 2 h and the addition of 330 ppm of cyclohexanol to the medium. This can be followed by further incubation at 30° C. for an additional period of time such as, for example, 2 h, 4 h or 20 h or other time intervals. The procedure for producing fermentation broths containing AA by culturing the E. coli cosmid clones designated 5B12, 5F5, 8F6 and 14D7 comprising a vector expressing the cyclohexanone monooxygenase encoded by SEQ ID NO: 1 from Acinetobacter strain SE19 in a growth medium comprising D-glucose and clyclohexanol is also described in U.S. Pat. No. 6,794,165, the subject matter of which is incorporated herein by reference.

Fermentation broths containing AA can also be produced with the Verdezyne Yeast strain available from Verdezyne, Inc. (Carslbad, Calif., USA) which was reported on Feb. 8, 2010 to produce AA when cultured in a medium (e.g., SD medium) comprising alkanes or other carbon sources such as sugars and plant-based oils.

Fermentation broths containing AA can also be produced from E. coli or other microorganisms transformed with nucleic acids encoding succinyl-CoA:acetyl-CoA acyl transferase; 3-hydroxyacyl-CoA dehydrogenase; 3-hydroxyadipyl-CoA dehydratase; 5-carboxy-2-pentenoyl-CoA reductase; adipyl-CoA synthetase, phosphotransadipylase/adipate kinase, adipyl-CoA transferase or adipyl-CoA hydrolase. Fermentation broths containing AA can further be produced from E. coli or other microorganisms transformed with nucleic acids encoding succinyl-CoA:acetyl-CoA acyl transferase; 3-oxoadipyl-CoA transferase; 3-oxoadipate reductase; 3-hydroxyadipate dehydratase; and 2-enoate reductase. Fermentation broths containing AA can also be produced from E. coli or other microorganisms transformed with nucleic acids encoding alpha-ketoadipyl-CoA synthetase, phosphotransketoadipylase/alpha-ketoadipate kinase or alpha-ketoadipyl-CoA:acetyl-CoA tranferase; 2-hydroxyadipyl-CoA dehydrogenase; 2-hydroxyadipyl-CoA dehydratase; 5-carboxy-2-penteoyl-CoA reductase; and adipyl-CoA synthetase, phosphotransadipylase/adipate kinase, adipyl-CoA:acetyl-CoA transferase or adipyl-CoA hydrolase. Fermentation broths containing AA can still further be produced from E. coli or other microorganisms transformed with nucleic acids encoding 2-hydroxyadipate dehydrogenase; 2-hydroxyadipyl-CoA synthetase, phosphotranshydroxyadipylase/2-hydroxyadipate kinase or 2-hydroxyadipyl-CoA:acetyl-CoA transferase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase.

Fermentations with E. coli or other microorganisms transformed with nucleic acids encoding these enzymes may be performed using a variety of different carbon sources under standard conditions in standard culture mediums (e.g., M9 minimal medium) and appropriate antibiotic or nutritional supplements necessary to maintain the transformed phenotype. The procedure for producing fermentation broths containing AA by culturing E. coli or other microorganisms transformed with nucleic acids encoding these enzymes, appropriate growth mediums and carbon sources are also described in US 2009/0305364, the subject matter of which is incorporated herein by reference.

Procedures for producing fermentation broths containing dicarboxylic acids such as AA by culturing Saccharomyces cerevisiae and other strains, microorganism strains, appropriate growth mediums and carbon sources are also described in WO 2010/003728, the subject matter of which is incorporated herein by reference.

A fermentable carbon source (e.g., carbohydrates and sugars), optionally a source of nitrogen and complex nutrients (e.g., corn steep liquor), additional media components such as vitamins, salts and other materials that can improve cellular growth and/or product formation, and water may be fed to the growth vessel 12 for growth and sustenance of the microbial culture. Typically, the microbial culture is grown under aerobic conditions provided by sparging an oxygen-rich gas (e.g., air or the like). Typically, an acid (e.g., sulphuric acid or the like) and ammonium hydroxide are provided for pH control during the growth of the microbial culture.

In one example (not shown), the aerobic conditions in growth vessel 12 (provided by sparging an oxygen-rich gas) are switched to anaerobic conditions by changing the oxygen-rich gas to an oxygen-deficient gas (e.g., $CO_2$ or the like). The anaerobic environment may trigger bioconversion of the fermentable carbon source to AA in situ in growth vessel 12. Ammonium hydroxide is provided for pH control during bioconversion of the fermentable carbon source to AA. The AA that is produced is at least partially if not totally neutralized to DAA due to the presence of the ammonium hydroxide, leading to the production of a broth comprising DAA. The addition of $CO_2$ may provide an additional source of carbon for the production of AA.

In another example, the contents of growth vessel 12 may be transferred via stream 14 to a separate bioconversion vessel 16 for bioconversion of a carbohydrate source to AA. An oxygen-deficient gas (e.g., $CO_2$ or the like) is sparged in bioconversion vessel 16 to provide anaerobic conditions that trigger production of AA. Ammonium hydroxide is provided for pH control during bioconversion of the carbohydrate source to AA. Due to the presence of the ammonium hydroxide, the AA produced is at least partially neutralized to DAA, leading to production of a broth that comprises DAA. The addition of $CO_2$ may provide an additional source of carbon for production of AA.

In yet another example, the bioconversion may be conducted at relatively low pH (e.g., 3-6). A base (ammonium hydroxide or ammonia) may be provided for pH control during bioconversion of the carbohydrate source to AA. Depending of the desired pH, due to the presence or lack of the ammonium hydroxide, either AA is produced or the AA produced is at least partially neutralized to MAA, DAA or a mixture comprising AA, MAA and/or DAA. Thus, the AA produced during bioconversion can be subsequently neutralized, optionally in an additional step, by providing either ammonia or ammonium hydroxide leading to a broth comprising DAA. As a consequence, a "DAA-containing fermentation broth" generally means that the fermentation broth comprises DAA and possibly any number of other components such as MAA and/or AA, whether added and/or produced by bioconversion or otherwise. Similarly, a "MAA-containing fermentation broth" generally means that the fermentation broth comprises MAA and possibly any number of other components such as DAA and/or AA, whether added and/or produced by bioconversion or otherwise.

The broth resulting from the bioconversion of the fermentable carbon source (in either growth vessel 12 or bioconversion vessel 16, depending on where the bioconversion takes place), typically contains insoluble solids such as cellular biomass and other suspended material, which are transferred via stream 18 to clarification apparatus 20 before distillation. Removal of insoluble solids clarifies the broth. This reduces or prevents fouling of subsequent distillation equipment. The insoluble solids can be removed by any one of several solid-liquid separation techniques, alone or in combination, including but not limited to centrifugation and filtration (including, but not limited to ultra-filtration, micro-filtration or depth filtration). The choice of filtration can be made using techniques known in the art. Soluble inorganic compounds can be removed by any number of known methods such as, but not limited to, ion-exchange, physical adsorption and the like.

An example of centrifugation is a continuous disc stack centrifuge. It may be useful to add a polishing filtration step following centrifugation such as dead-end or cross-flow filtration that may include the use of a filter aid such as diatomaceous earth or the like, or more preferably ultra-filtration or micro-filtration. The ultra-filtration or micro-filtration membrane can be ceramic or polymeric, for example. One example of a polymeric membrane is SelRO MPS-U20P (pH stable ultra-filtration membrane) manufactured by Koch Membrane Systems (850 Main Street, Wilmington, Mass., USA). This is a commercially available polyethersulfone membrane with a 25,000 Dalton molecular weight cut-off which typically operates at pressures of 0.35 to 1.38 MPa (maximum pressure of 1.55 MPa) and at temperatures up to 50° C. Alternatively, a filtration step may be employed alone using ultra-filtration or micro-filtration.

The resulting clarified DAA-containing broth or MAA-containing broth, substantially free of the microbial culture and other solids, is transferred via stream 22 to distillation apparatus 24.

The clarified distillation broth should contain DAA in an amount that is at least a majority of, preferably at least about 70 wt %, more preferably 80 wt % and most preferably at least about 90 wt % of all the diammonium dicarboxylate salts in the broth. The concentration of DAA and/or MAA as a weight percent (wt %) of the total dicarboxylic acid salts in the fermentation broth can be determined by high pressure liquid chromatography (HPLC) or other known means.

Water and ammonia are removed from distillation apparatus 24 as an overhead, and at least a portion is optionally recycled via stream 26 to bioconversion vessel 16 (or growth vessel 12 operated in the anaerobic mode).

The specific distillation temperature and pressure are not critical as long as the distillation is carried out in a way that ensures that the distillation overhead contains water and ammonia, and the distillation bottoms comprises at least some AA and at least about 20 wt % water. A more preferred amount of water is at least about 30 wt % and an even more preferred amount is at least about 40 wt %. The rate of ammonia removal from the distillation step increases with increasing temperature and also can be increased by injecting steam (not shown) during distillation. The rate of ammonia removal during distillation may also be increased by conducting distillation under a vacuum or by sparging the distillation apparatus with a non-reactive gas such as air, nitrogen or the like.

Removal of water during the distillation step can be enhanced by the use of an organic azeotroping agent such as toluene, xylene, methylcyclohexane, methyl isobutyl ketone, cyclohexane, heptane or the like, provided that the bottoms contains at least about 20 wt % water. If the distillation is carried out in the presence of an organic agent capable of forming an azeotrope consisting of the water and the agent, distillation produces a biphasic bottoms that comprises an aqueous phase and an organic phase, in which case the aqueous phase can be separated from the organic phase, and the aqueous phase used as the distillation bottoms. By-products such as adipimide and adipamide are substantially avoided provided the water level in the bottoms is maintained at a level of at least about 30 wt %.

A preferred temperature for the distillation step is in the range of about 50° C. to about 300° C., depending on the pressure. A more preferred temperature range is about 150° C. to about 240° C., depending on the pressure. A distillation temperature of about 170° C. to about 230° C. is preferred. "Distillation temperature" refers to the temperature of the bottoms (for batch distillations this may be the temperature at the time when the last desired amount of overhead is taken).

Adding a water miscible organic solvent or an ammonia separating solvent facilitates deammoniation over a variety of distillation temperatures and pressures as discussed above. Such solvents include aprotic, bipolar, oxygen-containing solvents that may be able to form passive hydrogen bonds. Examples include, but are not limited to, diglyme, triglyme, tetraglyme, sulfoxides such as dimethylsulfoxide (DMSO), amides such as dimethylformamide (DMF) and dimethylacetamide, sulfones such as dimethylsulfone, gamma-butyrolactone (GBL), sulfolane, polyethyleneglycol (PEG), butoxytriglycol, N-methylpyrolidone (NMP), ethers such as dioxane, methyl ethyl ketone (MEK) and the like. Such solvents aid in the removal of ammonia from the DAA or MAA in the clarified broth. Regardless of the distillation technique, it is important that the distillation be carried out in a way that ensures that at least some MAA and at least about 20 wt % water remain in the bottoms and even more advantageously at least about 30 wt %. The distillation can be performed at atmospheric, sub-atmospheric or super-atmospheric pressures.

Under other conditions such as when the distillation is conducted in the absence of an azeotropic agent or ammonia separating solvent, the distillation is conducted at super atmospheric pressure at a temperature of greater than 100° C. to about 300° C. to form an overhead that comprises water and ammonia and a liquid bottoms that comprises AA and at least about 20 wt % water. Super atmospheric pressure typically falls within a range of greater than ambient atmosphere up to and including about 25 atmospheres. Advantageously the amount of water is at least about 30 wt %.

The distillation can be a one-stage flash, a multistage distillation (i.e., a multistage column distillation) or the like. The one-stage flash can be conducted in any type of flasher (e.g., a wiped film evaporator, thin film evaporator, thermosiphon flasher, forced circulation flasher and the like). The multistages of the distillation columns can be achieved by using trays, packing or the like. The packing can be random packing (e.g., Raschig rings, Pall rings, Berl saddles and the like) or structured packing (e.g., Koch-Sulzer packing, Intalox packing, Mellapak and the like). The trays can be of any design (e.g., sieve trays, valve trays, bubble-cap trays and the like). The distillation can be performed with any number of theoretical stages.

If the distillation apparatus is a column, the configuration is not particularly critical, and the column can be designed using well known criteria. The column can be operated in either stripping mode, rectifying mode or fractionation mode. Distillation can be conducted in either batch, semi-continuous or continuous mode. In the continuous mode, the broth is fed continuously into the distillation apparatus, and the overhead and bottoms are continuously removed from the apparatus as they are formed. The distillate from distillation is an ammonia/water solution, and the distillation bottoms is a liquid, aqueous solution of MAA and AA, which may also contain other fermentation by-product salts (i.e., ammonium acetate, ammonium formate, ammonium lactate and the like) and color bodies.

The distillation bottoms can be transferred via stream 28 to cooling apparatus 30 and cooled by conventional techniques. Cooling technique is not critical. A heat exchanger (with heat recovery) can be used. A flash vaporization cooler can be used to cool the bottoms down to about 15° C. Cooling to 15° C. typically employs a refrigerated coolant such as, for example, glycol solution or, less preferably, brine. A concentration step can be included prior to cooling to help increase product yield. Further, both concentration and cooling can be combined using known methods such as vacuum evaporation and heat removal using integrated cooling jackets and/or external heat exchangers.

Figure 2:
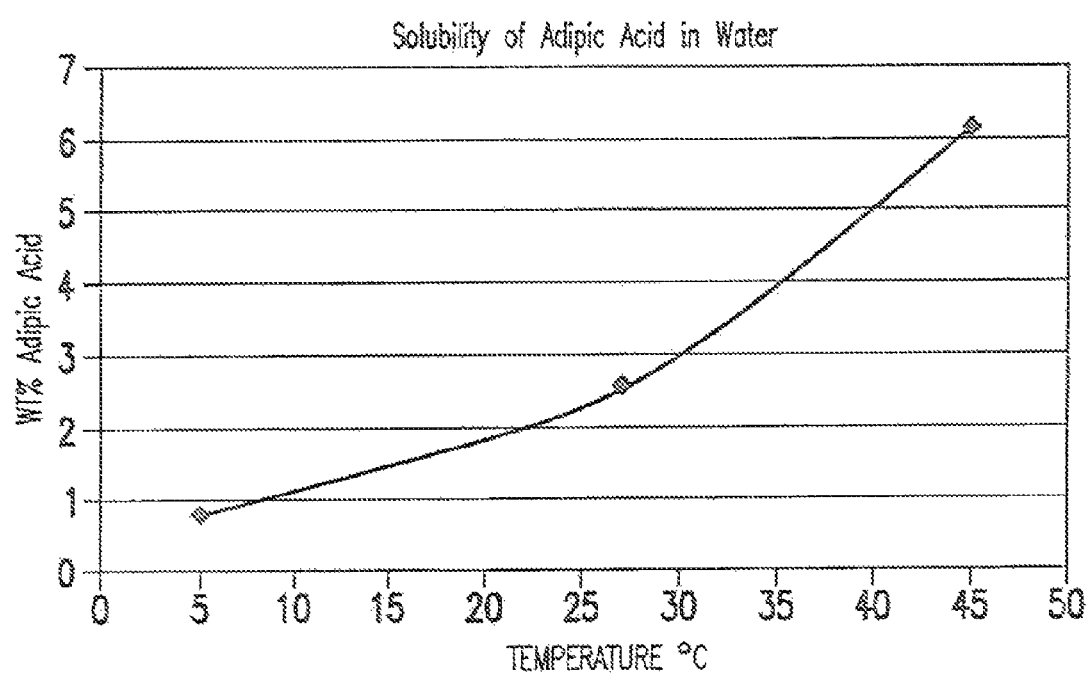
FIG. 2 is a graph showing the solubility of AA in water as a function of temperature.

We found that the presence of some MAA in the liquid bottoms facilitates cooling-induced separation of the bottoms into a liquid portion in contact with a solid portion that at least "consists essentially" of AA (meaning that the solid portion is at least substantially pure crystalline AA) by reducing the solubility of AA in the liquid, aqueous, MAA-containing bottoms. FIG. 2 illustrates the solubility of AA in water. We discovered, therefore, that AA can be more completely crystallized out of an aqueous solution if some MAA is also present in that solution. A preferred concentration of MAA in such a solution is about 20 wt %. A more preferred concentration of MAA in such a solution is in the ppm to about 3 wt % range. This phenomenon allows crystallization of AA (i.e., formation of the solid portion of the distillation bottoms) at temperatures higher than those that would be required in the absence of MAA.

The distillation bottoms is fed via stream 32 to separator 34 for separation of the solid portion from the liquid portion. Separation can be accomplished via pressure filtration (e.g., using Nutsche or Rosenmond type pressure filters), centrifugation and the like. The resulting solid product can be recovered as product 36 and dried, if desired, by standard methods.

After separation, it may be desirable to treat the solid portion to ensure that no liquid portion remains on the surface(s) of the solid portion. One way to minimize the amount of liquid portion that remains on the surface of the solid portion is to wash the separated solid portion with water and dry the resulting washed solid portion (not shown). A convenient way to wash the solid portion is to use a so-called "basket centrifuge" (not shown). Suitable basket centrifuges are available from The Western States Machine Company (Hamilton, Ohio, USA).

The liquid portion of the distillation bottoms 34 (i.e., the mother liquor) may contain remaining dissolved AA, any unconverted MAA, any fermentation by-products such as ammonium acetate, lactate, or formate, and other minor impurities. This liquid portion can be fed via stream 38 to a downstream apparatus 40. In one instance, apparatus 40 may be a means for making a de-icer by treating in the mixture with an appropriate amount of potassium hydroxide, for example, to convert the ammonium salts to potassium salts. Ammonia generated in this reaction can be recovered for reuse in the bioconversion vessel 16 (or growth vessel 12 operating in the anaerobic mode). The resulting mixture of potassium salts is valuable as a de-icer and anti-icer.

The mother liquor from the solids separation step 34 can be recycled (or partially recycled) to distillation apparatus 24 via stream 42 to further enhance recovery of AA, as well as further convert MAA to AA.

The solid portion of the cooling-induced crystallization is substantially pure AA and is, therefore, useful for the known utilities of AA.

HPLC can be used to detect the presence of nitrogen-containing impurities such as adipamide and adipimide. The purity of AA can be determined by elemental carbon and nitrogen analysis. An ammonia electrode can be used to determine a crude approximation of AA purity.

Depending on the circumstances and various operating inputs, there are instances when the fermentation broth may be a clarified MAA-containing fermentation broth or a clarified AA-containing fermentation broth. In those circumstances, it can be advantageous to add MAA, DAA and/or AA and, optionally, ammonia and/or ammonium hydroxide to those fermentation broths to facilitate the production of substantially pure AA. For example, the operating pH of the fermentation broth may be oriented such that the broth is a MAA-containing broth or a AA-containing broth. MAA, DAA, AA, ammonia and/or ammonium hydroxide may be added to those broths to attain a broth pH preferably less than 6 to facilitate production of the above-mentioned substantially pure AA. In one particular form, it is especially advantageous to recycle AA, MAA and water from the liquid bottoms resulting from the distillation step 24 into the fermentation broth and/or clarified fermentation broth. In referring to the MAA-containing broth, such broth generally means that the fermentation broth comprises MAA and possibly any number of other components such as DAA and/or AA, whether added and/or produced by bioconversion or otherwise.

Figure 3:
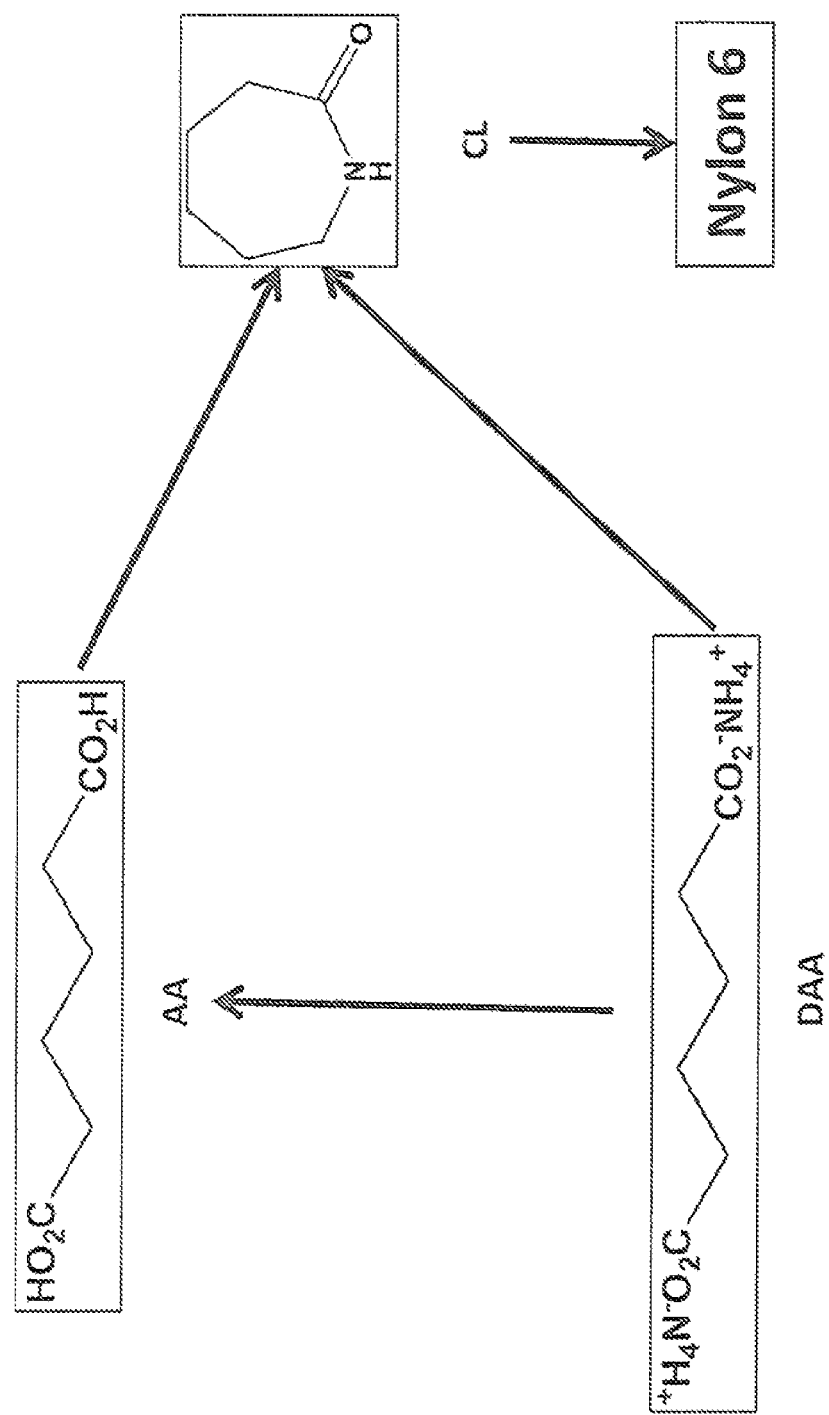
FIG. 3. is a flow diagram for producing CL and at least one derivative of CL from AA.

Streams comprising AA as presented in FIG. 3 may be contacted with various reactant(s) and catalyst(s) at selected temperatures and pressures to produce CL. The AA may be dissolved or suspended in water or a solvent such as dioxane for use in downstream reactions such as conversion to CL. It is possible to convert such solutions or suspensions of AA (and MAA to DAA) by addition of an ammonia source (e.g., $NH_3$ or $NH_4OH$). Thus, solutions or suspensions of AA may be dehydrated to form an amide of AA followed by hydrogenation of the amide to form CL.

CL may be produced by various methods such as methods disclosed in GB 778,253, for example. GB 778,253 discloses that AA, adipic acid diamide or diamide-forming derivatives of AA can be converted into CL in a single stage. AA, its diamide or a diamide-forming derivative thereof may be treated as a liquid with hydrogen at elevated temperature, preferably not exceeding 220° C., and under pressure in the presence of ammonia and a hydrogenation catalyst. The process does not produce hexamethylene diamine (HMD) as might be expected, but CL with ammonia removed. Adipic acid diamide or its diammonium salt can be used as the starting material or AA or a diamide-forming derivative of AA which, like the di-acid chloride or a di-ester, is converted by adding ammonia into adipic acid diamide and then to CL. The subject matter and content of the above mentioned GB 778,253 is incorporated herein by reference.

Although it is possible to produce CL alone as mentioned above, it is also possible to coproduce CL with other useful materials such as, for example, HMD. One example may be found in JP 49/019250, the subject matter of which is incorporated herein by reference. CL and HMD can be produced simultaneously by treating either AA, adipamide, DAA or an alkyl adipate with $NH_3$ and $H_2$ in the presence of Ru metal catalyst. An example discloses that AA 36.5 g, $H_2O$ 4.5 g, liq. $NH_3$ 255 g and 20 g active C containing 5% Ru were treated for 4 hours under $H_2$ at 60 kg/cm² gauge at 240° C. This resulted in 9.2 g CL and 7.7 g HMD. The distillation residues containing AA and its derivatives, e.g., aminocaproic acid, were recycled to provide an additional 4.4 g CL and 3.7 g HMD.

Further, it is possible to produce CL from an adipamide such as diamide or the monoamide of AA as also disclosed in GB 778,253. For example, GB 778,253 treated a suspension of 180 g of adipic diamide in about 3 liters of technical diozan with 45 g of Raney nickel in a 5 liter stirring autoclave at 220° C. under 250 atm hydrogen pressure. The pressure was increased to about 380 atm. The heating was discontinued after 15 hours. The autoclave was cooled and the product separated from the catalyst. After distilling off dioxin, a light oil was fractionated in a vacuum. After a few drops of first runnings, CL distilled off in a boiling range of 120° C. to 130° C./6 mm and crystallized with a melting point of 69° C. The CL could then be polymerized by known methods to a polyamide having a melting point of about 220° C.

Hydrogenation catalysts for the conversion of AA to CL may be promoted to augment the activity or selectivity of the catalyst. The promoter may be incorporated into the catalyst during any step in the chemical processing of the catalyst constituent. The chemical promoter generally enhances the physical or chemical function of the catalyst agent, but can also be added to retard undesirable side reactions. Suitable promoters include, for example, metals selected from tin, zinc, copper, rhenium, gold, silver, and combinations thereof. Other promoters that can be used are elements selected from Group I and Group II of the Periodic Table.

The catalyst may be supported or unsupported. A supported catalyst is one in which the active catalyst agent is deposited on a support material by a number of methods such as spraying, soaking or physical mixing, followed by drying, calcination and, if necessary, activation through methods such as reduction or oxidation. Materials frequently used as a support are porous solids with high total surface areas (external and internal) which can provide high concentrations of active sites per unit weight of catalyst. The catalyst support may enhance the function of the catalyst agent. A supported metal catalyst is a supported catalyst in which the catalyst agent is a metal.

A catalyst that is not supported on a catalyst support material is an unsupported catalyst. An unsupported catalyst may be platinum black or a Raney® (W.R. Grace & Co., Columbia, Md.) catalyst, for example. Raney® catalysts have a high surface area due to selectively leaching an alloy containing the active metal(s) and a leachable metal (usually aluminum). Raney® catalysts have high activity due to the higher specific area and allow the use of lower temperatures in hydrogenation reactions. The active metals of Raney® catalysts include nickel, copper, cobalt, iron, rhodium, ruthenium, rhenium, osmium, iridium, platinum, palladium, compounds thereof and combinations thereof.

Promoter metals may also be added to the base Raney® metals to affect selectivity and/or activity of the Raney® catalyst. Promoter metals for Raney® catalysts may be selected from transition metals from Groups IIIA through VIIIA, IB and IIB of the Periodic Table of the Elements. Examples of promoter metals include chromium, molybdenum, platinum, rhodium, ruthenium, osmium, and palladium, typically at about 2% by weight of the total metal.

The catalyst support can be any solid, inert substance including, but not limited to, oxides such as silica, alumina and titania; barium sulfate; calcium carbonate; and carbons. The catalyst support can be in the form of powder, granules, pellets or the like.

A preferred support material may be selected from the group consisting of carbon, alumina, silica, silica-alumina, silica-titania, titania, titania-alumina, barium sulfate, calcium carbonate, strontium carbonate, compounds thereof and combinations thereof. Supported metal catalysts can also have supporting materials made from one or more compounds. More preferred supports are carbon, titania and alumina. Further preferred supports are carbons with a surface area greater than about 100 m²/g. A further preferred support is carbon with a surface area greater than about 200 m²/g. Preferably, the carbon has an ash content that is less than about 5% by weight of the catalyst support. The ash content is the inorganic residue (expressed as a percentage of the original weight of the carbon) which remains after incineration of the carbon.

A preferred content of the metal catalyst in the supported catalyst may be from about 0.1% to about 20% of the supported catalyst based on metal catalyst weight plus the support weight. A more preferred metal catalyst content range is from about 1% to about 10% of the supported catalyst.

Combinations of metal catalyst and support system may include any one of the metals referred to herein with any of the supports referred to herein. Preferred combinations of metal catalyst and support include palladium on carbon, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina and ruthenium on silica.

Further preferred combinations of metal catalyst and support include ruthenium on carbon, ruthenium on alumina, palladium on carbon, palladium on alumina, palladium on titania, platinum on carbon, platinum on alumina, rhodium on carbon, and rhodium on alumina.

Typically, the hydrogenation reactions are performed at temperatures from about 100° C. to about 500° C. in reactors maintained at pressures from about 6 to about 20 MPa.

The method of using the catalyst to hydrogenate an AA or MAA containing feed can be performed by various modes of operation generally known in the art. Thus, the overall hydrogenation process can be performed with a fixed bed reactor, various types of agitated slurry reactors, either gas or mechanically agitated, or the like. The hydrogenation process can be operated in either a batch or continuous mode, wherein an aqueous liquid phase containing the precursor to hydrogenate is in contact with a gaseous phase containing hydrogen at elevated pressure and the particulate solid catalyst.

Temperature, solvent, catalyst, reactor configuration, pressure and mixing rate are all parameters that affect the conversion and selectivity. The relationships among these parameters may be adjusted to effect the desired conversion, reaction rate, and selectivity in the reaction of the process.

A preferred temperature may be from about 25° C. to 500° C., more preferably from about 100° C. to about 400° C., and most preferred from about 150° C. to 400° C. The pressure may preferably be about 0.5 to about 40 MPa.

The processes and/or conversion may be carried out in batch, sequential batch (i.e., a series of batch reactors) or in continuous mode in any of the equipment customarily employed for continuous processes. The condensate water formed as the product of the reaction is removed by separation methods customarily employed for such separations.

It is possible to convert CL to polyamides such as Nylon 6 as shown in FIG. 4. One process for such a conversion is disclosed in JP 2008/144075, the subject matter of which is incorporated herein by reference. The process comprises polymerizing a raw material composition containing at least CL and water. The raw material composition then contains, as an end-capping agent, any one selected from among the three combinations consisting of (a) at least one kind of monocarboxylic acid compound and at least one kind of primary or secondary monoamine compound, (b) at least one kind of monocarboxylic acid compound and at least one kind of primary diamine compound or secondary diamine compound and (c) at least one kind of dicarboxylic acid compound and at least one kind of primary monoamine compound or secondary diamine compound. Heat may be applied to the raw material composition at a temperature of at least about 240° C. to initiate polymerization.

EXAMPLES

Our processes are illustrated by the following non-limiting representative examples.

The use of a synthetic DAA solution is believed to be a good model for the behavior of an actual broth in our processes because of the solubility of the typical fermentation by-products found in actual broth. The major by-products produced during fermentation are ammonium acetate, ammonium lactate and ammonium formate. Ammonium acetate, ammonium lactate and ammonium formate are significantly more soluble in water than AA, and each is typically present in the broth at less than 10% of the DAA concentration. In addition, even when the acids (acetic, formic and lactic acids) were formed during the distillation step, they are miscible with water and will not crystallize from water. This means that the AA reaches saturation and crystallizes from solution (i.e., forming the solid portion), leaving the acid impurities dissolved in the mother liquor (i.e., the liquid portion).

Example 1

This example shows the conversion of DAA to MAA.

A 1-L round bottom flask was charged with 800 g of a synthetic 4.5% DAA solution. The flask was fitted with a five tray Oldershaw section which was capped with a distillation head. The distillate was collected in an ice cooled receiver. The contents of the flask were heated with a heating mantel and stirred with a magnetic stirrer. Distillation was started and 719.7 g of distillate collected. Titration of the distillate revealed it was a 0.29% ammonia solution (i.e. an about 61% conversion of DAA to MAA). The hot residue (76 g) was discharged from the flask and placed in an Erlenmeyer flask and slowly cooled to room temperature while stirring over a weekend. The contents were then cooled to 15° C. for 60 minutes and then cooled to 10° C. for 60 minutes and finally 5° C. for 60 minutes while stirring. The solids were filtered and dried in a vacuum oven for 2 hour at 75° yielding 16.2 g. Analysis of the solids for ammonia content by ammonia electrode indicated it was approximately a 1:1 molar ratio of ammonia and AA.

Example 2

This example shows the conversion of MAA to AA.

A 300 mL Parr autoclave was charged with 80 g of synthetic MAA and 124 g of water. The autoclave was sealed and the contents stirred and heated to about 200° C. (autogenic pressure was about 203 psig). Once the contents reached temperature, water was then fed to the autoclave at a rate of about 2 g/min and vapor was removed from the autoclave at a rate of about 2 g/min by means of a back pressure regulator. The vapor exiting the autoclave was condensed and collected in a receiver. The autoclave was run under these conditions until a total of 1210 g of water had been fed and a total of 1185 g of distillate collected. The contents of the autoclave (209 g) were partially cooled and discharged from the reactor. The slurry was allowed to stand stirring at room temperature over night in an Erlenmeyer flask. The slurry was then filtered and the solids rinsed with 25 g of water. The moist solids were dried in a vacuum oven at 75° C. for 1 hr yielding 59 g of AA product. Analysis via an ammonium ion electrode revealed 0.015 mmole ammonium ion/g of solid. The melting point of the recovered solid was 151 to 154° C.

Example 3

This example shows the conversion of DAA to MAA in the presence of a solvent.

A beaker was charged with 36.8 g of distilled water and 19.7 g of concentrated ammonium hydroxide. Then 23.5 g of adipic acid was slowly added. The mixture was stirred forming a clear solution which was then placed in a 500 mL round bottom flask which contained a stir bar. Triglyme (80 g) was then added to the flask. The flask was then fitted with a 5 tray 1" Oldershaw column section which was topped with a distillation head. The distillation head was fitted with an ice bath cooled receiver. The distillation flask was also fitted with an addition funnel which contained 150 g of distilled water. The contents were then stirred and heated with a heating mantel. When distillate began to come over the water in the addition funnel was added dropwise to the flask at the same rate as the distillate take-off. The distillation was stopped when all of the water in the addition funnel had been added. A total of 158 g of distillate had been collected. Titration of the distillate revealed a 1.6% ammonia content. This is equivalent to 46% of the charged ammonia. In other words the residue is a 91/9 mixture of monoammonium adipate/diammonium adipate. After cooling to room temperature, the residue was place in a 250 mL Erlenmeyer flask and slowly cooled to 5° C. while stirring. The slurry was filtered and the wet crystals were then dried in a vacuum oven for 2 hours yielding 5.5 g of solids. Analysis of the solids indicated essentially a one to one ratio of ammonium ion to adipate ion (i.e. monoammonium adipate).

Example 4

This example shows the conversion of MAA to AA in the presence of a solvent.

A beaker was charged with 46.7 g of distilled water and 9.9 g of concentrated ammonium hydroxide. Then 23.5 g of adipic acid was slowly added. The mixture was stirred forming a clear solution which was then placed in a 500 mL round bottom flask which contained a stir bar. Triglyme (80 g) was then added to the flask. The flask was then fitted with a 5 tray 1" Oldershaw column section which was topped with a distillation head. The distillation head was fitted with an ice bath cooled receiver. The distillation flask was also fitted with an addition funnel which contained 1800 g of distilled water. The contents were then stirred and heated with a heating mantel. When distillate began to come over the water in the addition funnel was added dropwise to the flask at the same rate as the distillate take-off. The distillation was stopped when all of the water in the addition funnel had been added. A total of 1806.2 g of distillate had been collected. Titration of the distillate revealed a 0.11% ammonia content. This is equivalent to 72% of the charged ammonia. In other words the residue is a 72/28 mixture of adipic acid/monoammonium adipate. The residue was then placed in an Erlenmeyer flask and cooled to 0° C. while stirring and allowed to stand for 1 hr. The slurry was filtered yielding 18.8 g of a wet cake and 114.3 g of mother liquor. The solids were then dried under vacuum at 80° C. for 2 hrs yielding 13.5 g of solids. The solids were then dissolved in 114 g of hot water and then cooled to 5° C. and held stirring for 45 minutes. The slurry was filtered yielding 13.5 g of wet solids and 109.2 g of mother liquor. The solids were dried under vacuum at 80° C. for 2 hrs yielding 11.7 g of dried solids. Analysis of the solids revealed an ammonium ion content of 0.0117 mmol/g (i.e. essentially pure adipic acid).

Although our processes have been described in connection with specific steps and forms thereof, it will be appreciated that a wide variety of equivalents may be substituted for the specified elements and steps described herein without departing from the spirit and scope of this disclosure as described in the appended claims.

The invention claimed is:

1. A process for producing CL from a clarified DAA-containing fermentation broth or MAA-containing fermentation broth comprising:
   (a) distilling the broth under greater than ambient pressure at a temperature of >100° C. to about 300° C. to form an overhead that comprises water and ammonia, and a liquid bottoms that comprises AA and at least about 20 wt % water;
   (b) cooling and/or evaporating the bottoms to attain a temperature and composition sufficient to cause the bottoms to separate into a liquid portion and a solid portion that is substantially pure AA;
   (c) separating the solid portion from the liquid portion; and
   (d) contacting at least a part of the solid portion with hydrogen, optionally in the presence of a solvent, in the presence of a hydrogenation catalyst and an ammonia source, at a temperature of about 25° C. to about 500° C. and a pressure of about 0.5 to about 40 MPa to produce the CL.

2. A process for producing CL from a clarified DAA-containing fermentation broth or MAA-containing fermentation broth comprising:
   (a) adding an ammonia separating solvent and/or a water azeotroping solvent to the broth;
   (b) distilling the broth at a temperature and pressure sufficient to form an overhead that comprises water and ammonia, and a liquid bottoms that comprises AA and at least about 20 wt % water;
   (c) cooling and/or evaporating the bottoms to attain a temperature and composition sufficient to cause the bottoms to separate into a liquid portion and a solid portion that is substantially pure AA;
   (d) separating the solid portion from the liquid portion; and (e) contacting at least a part of the solid portion with hydrogen, optionally in the presence of a solvent, in the presence of a hydrogenation catalyst and an ammonia source, at a temperature of about 25° C. to about 500° C. and a pressure of about 0.5 to about 40 MPa to produce the CL.

3. The process of claim 1, wherein producing the CL comprises dehydrating at least part of the solid portion in the presence of an ammonia source to produce an amide of AA followed by hydrogenation of the amide to form CL.

4. The process of claim 1, further comprising converting the CL to NYLON 6.

5. The process of claim 1, wherein the fermentation broth is obtained by fermenting a carbon source in the presence of a microorganism selected from the group consisting of *Candida tropicalis* (Castellani) Berkhout, anamorph strain OH23 having ATCC accession number 24887; *E. coli* strain AB2834/pKD136/pKD8.243 A/pKD8.292 having ATCC accession number 69875; *E. coli* cosmid clone 5B12 comprising a vector expressing the cyclohexanone monoxygenase encoded by SEQ ID NO: 1, *E. coli* cosmid clone 5F5 comprising a vector expressing the cyclohexanone monoxygenase encoded by SEQ ID NO: 1; *E. coli* cosmid clone 8F6 comprising a vector expressing the cyclohexanone monoxygenase encoded by SEQ ID NO: 1; *E. coli* cosmid clone 14D7 comprising a vector expressing the cyclohexanone monoxygenase encoded by SEQ ID NO: 1; and Verdezyne Yeast.

6. The process of claim 2, wherein distilling the broth is carried out in the presence of an ammonia separating solvent which is at least one selected from the group consisting of diglyme, triglyme, tetraglyme, sulfoxides, amides, sulfones, polyethyleneglycol (PEG), butoxytriglycol, N-methylpyrolidone (NMP), ethers, and methyl ethyl ketone (MEK) or in the presence of a water azeotroping solvent which is at least one selected from the group consisting of toluene, xylene, methylcyclohexane, methyl isobutyl ketone, hexane, cyclohexane and heptane.

7. The process of claim 2, wherein producing the CL comprises dehydrating at least part of the solid portion in the presence of an ammonia source to produce an amide of AA followed by hydrogenation of the amide to form CL.

8. The process of claim 2, further comprising converting the CL to NYLON 6.

9. The process of claim 3, further comprising converting the CL to NYLON 6.

10. The process of claim 7, further comprising converting the CL to NYLON 6.

11. The process of claim 2, wherein the fermentation broth is obtained by fermenting a carbon source in the presence of a microorganism selected from the group consisting of *Candida tropicalis* (Castellani) Berkhout, anamorph strain OH23 having ATCC accession number 24887; *E. coli* strain AB2834/pKD136/pKD8.243 A/pKD8.292 having ATCC accession number 69875; *E. coli* cosmid clone 5B12 comprising a vector expressing the cyclohexanone monoxygenase encoded by SEQ ID NO: 1, *E. coli* cosmid clone 5F5 comprising a vector expressing the cyclohexanone monoxygenase encoded by SEQ ID NO 1; *E. coli* cosmid clone 8F6 comprising a vector expressing the cyclohexanone monoxygenase encoded by SEQ ID NO: 1; *E. coli* cosmid clone 14D7 comprising a vector expressing the cyclohexanone monoxygenase encoded by SEQ ID NO: 1; and Verdezyne Yeast.

* * * * *

SEQUENCE LISTING

```
<160> NUMBER OF SEQ ID NOS: 2

<210> SEQ ID NO 1
<211> LENGTH: 1644
<212> TYPE: DNA
<213> ORGANISM: Acinetobacter sp.

<400> SEQUENCE: 1
atggagatta tcatgtcaca aaaaatggat tttgatgcta tcgtgattgg tggtggtttt      60
ggcggacttt atgcagtcaa aaaattaaga gacgagctcg aacttaaggt tcaggctttt     120
gataaagcca cggatgtcgc aggtacttgg tactggaacc gttacccagg tgcattgtcg     180
gatacagaaa cccacctcta ctgctattct tgggataaag aattactaca atcgctagaa     240
atcaagaaaa atatgtgca aggccctgat gtacgcaagt atttacagca agtggctgaa     300
aagcatgatt taaagaagag ctatcaattc aataccgcgg ttcaatcggc tcattacaac     360
gaagcagatg ccttgtggga agtcaccact gaatatggtg ataagtacac ggcgcgtttc     420
ctcatcactg ctttaggctt attgtctgcg cctaacttgc caaacatcaa aggcattaat     480
cagtttaaag gtgagctgca tcataccagc cgctggccag atgacgtaag ttttgaaggt     540
aaacgtgtcg gcgtgattgg tacgggttcc accggtgttc aggttattac ggctgtggca     600
cctctggcta aacacctcac tgtcttccag cgttctgcac aatacagcgt tccaattggc     660
aatgatccac tgtctgaaga agatgttaaa aagatcaaag acaattatga caaaatttgg     720
gatggtgtat ggaattcagc ccttgccttt ggcctgaatg aaagcacagt gccagcaatg     780
agcgtatcag ctgaagaacg caaggcagtt tttgaaaagg catggcaaac aggtggcggt     840
ttccgtttca tgtttgaaac tttcggtgat attgccacca atatggaagc caatatcgaa     900
gcgcaaaatt tcattaaggg taaaattgct gaaatcgtca aagatccagc cattgcacag     960
```

```
aagcttatgc cacaggattt gtatgcaaaa cgtccgttgt gtgacagtgg ttactacaac    1020
acctttaacc gtgacaatgt ccgtttagaa gatgtgaaag ccaatccgat tgttgaaatt    1080
accgaaaacg gtgtgaaact cgaaaatggc gatttcgttg aattagacat gctgatatgt    1140
gccacaggtt ttgatgccgt cgatggcaac tatgtgcgca tggacattca aggtaaaaac    1200
ggcttggcca tgaaagacta ctggaaagaa ggtccgtcga gctatatggg tgtcaccgta    1260
aataactatc aaacatgttt catggtgctt ggaccgaatg gccgtttac caacctgccg     1320 ccatcaattg aatcacaggt ggaatggatc agtgatacca ttcaatacac ggttgaaaac    1380
aatgttgaat ccattgaagc gacaaaagaa gcggaagaac aatggactca aacttgcgcc    1440
aatattgcgg aaatgacctt attccctaaa gcgcaatcct ggattttgg tgcgaatatc     1500 ccgggcaaga aaacacggt ttacttctat ctcggtggtt taaaagaata tcgcagtgcg     1560
ctagccaact gcaaaaacca tgcctatgaa ggttttgata ttcaattaca acgttcagat    1620
atcaagcaac ctgccaatgc ctaa                                           1644
```

```
<210> SEQ ID NO 2
<211> LENGTH: 547
<212> TYPE: PRT
<213> ORGANISM: Acinetobacter sp.

<400> SEQUENCE: 2

Met Glu Ile Ile Met Ser Gln Lys Met Asp Phe Asp Ala Ile Val Ile
 1               5                  10                  15

Gly Gly Gly Phe Gly Gly Leu Tyr Ala Val Lys Lys Leu Arg Asp Glu
            20                  25                  30

Leu Glu Leu Lys Val Gln Ala Phe Asp Lys Ala Thr Asp Val Ala Gly
        35                  40                  45

Thr Trp Tyr Trp Asn Arg Tyr Pro Gly Ala Leu Ser Asp Thr Glu Thr
    50                  55                  60

His Leu Tyr Cys Tyr Ser Trp Asp Lys Glu Leu Leu Gln Ser Leu Glu
65                  70                  75                  80

Ile Lys Lys Lys Tyr Val Gln Gly Pro Asp Val Arg Lys Tyr Leu Gln
                85                  90                  95

Gln Val Ala Glu Lys His Asp Leu Lys Lys Ser Tyr Gln Phe Asn Thr
            100                 105                 110

Ala Val Gln Ser Ala His Tyr Asn Glu Ala Asp Ala Leu Trp Glu Val
        115                 120                 125

Thr Thr Glu Tyr Gly Asp Lys Tyr Thr Ala Arg Phe Leu Ile Thr Ala
    130                 135                 140

Leu Gly Leu Leu Ser Ala Pro Asn Leu Pro Asn Ile Lys Gly Ile Asn
145                 150                 155                 160

Gln Phe Lys Gly Glu Leu His His Thr Ser Arg Trp Pro Asp Asp Val
                165                 170                 175

Ser Phe Glu Gly Lys Arg Val Gly Val Ile Gly Thr Gly Ser Thr Gly
            180                 185                 190

Val Gln Val Ile Thr Ala Val Ala Pro Leu Ala Lys His Leu Thr Val
        195                 200                 205

Phe Gln Arg Ser Ala Gln Tyr Ser Val Pro Ile Gly Asn Asp Pro Leu
    210                 215                 220

Ser Glu Glu Asp Val Lys Lys Ile Lys Asp Asn Tyr Asp Lys Ile Trp
225                 230                 235                 240

Asp Gly Val Trp Asn Ser Ala Leu Ala Phe Gly Leu Asn Glu Ser Thr
                245                 250                 255
```

-continued

```
Val Pro Ala Met Ser Val Ser Ala Glu Glu Arg Lys Ala Val Phe Glu
            260                 265                 270
Lys Ala Trp Gln Thr Gly Gly Gly Phe Arg Phe Met Phe Glu Thr Phe
        275                 280                 285
Gly Asp Ile Ala Thr Asn Met Glu Ala Asn Ile Glu Ala Gln Asn Phe
        290                 295                 300
Ile Lys Gly Lys Ile Ala Glu Ile Val Lys Asp Pro Ala Ile Ala Gln
305                 310                 315                 320
Lys Leu Met Pro Gln Asp Leu Tyr Ala Lys Arg Pro Leu Cys Asp Ser
                325                 330                 335
Gly Tyr Tyr Asn Thr Phe Asn Arg Asp Asn Val Arg Leu Glu Asp Val
            340                 345                 350
Lys Ala Asn Pro Ile Val Glu Ile Thr Glu Asn Gly Val Lys Leu Glu
        355                 360                 365
Asn Gly Asp Phe Val Glu Leu Asp Met Leu Ile Cys Ala Thr Gly Phe
    370                 375                 380
Asp Ala Val Asp Gly Asn Tyr Val Arg Met Asp Ile Gln Gly Lys Asn
385                 390                 395                 400
Gly Leu Ala Met Lys Asp Tyr Trp Lys Glu Gly Pro Ser Ser Tyr Met
                405                 410                 415
Gly Val Thr Val Asn Asn Tyr Pro Asn Met Phe Met Val Leu Gly Pro
            420                 425                 430
Asn Gly Pro Phe Thr Asn Leu Pro Pro Ser Ile Glu Ser Gln Val Glu
        435                 440                 445
Trp Ile Ser Asp Thr Ile Gln Tyr Thr Val Glu Asn Asn Val Glu Ser
450                 455                 460
Ile Glu Ala Thr Lys Glu Ala Glu Glu Gln Trp Thr Gln Thr Cys Ala
465                 470                 475                 480
Asn Ile Ala Glu Met Thr Leu Phe Pro Lys Ala Gln Ser Trp Ile Phe
                485                 490                 495
Gly Ala Asn Ile Pro Gly Lys Lys Asn Thr Val Tyr Phe Tyr Leu Gly
            500                 505                 510
Gly Leu Lys Glu Tyr Arg Ser Ala Leu Ala Asn Cys Lys Asn His Ala
        515                 520                 525
Tyr Glu Gly Phe Asp Ile Gln Leu Gln Arg Ser Asp Ile Lys Gln Pro
    530                 535                 540
Ala Asn Ala
545
```